United States Patent [19]
Amann et al.

[11] Patent Number: 5,879,362
[45] Date of Patent: Mar. 9, 1999

[54] SURGICAL INSTRUMENT OF A CERAMIC MATERIAL AND PROCESS FOR FORMING SAME

[75] Inventors: Thomas Amann, Jestetten; Erich Tritt, Wutöschingen, both of Germany

[73] Assignee: SLG Kunststoff-Fabrik und Formenbau GmbH, Germany

[21] Appl. No.: 803,393

[22] Filed: Feb. 20, 1997

[30] Foreign Application Priority Data

Dec. 14, 1996 [DE] Germany ............... 196 52 097.5

[51] Int. Cl.$^6$ .................................................. A61B 17/00
[52] U.S. Cl. ............................................................ 606/167
[58] Field of Search ............... 606/39, 31, 41, 606/45, 46, 48, 142, 190, 167, 1

[56] References Cited

U.S. PATENT DOCUMENTS

| 4,693,986 | 9/1987 | Vit et al. ........................ 501/1 |
| 4,886,060 | 12/1989 | Wilksell ........................ 604/22 X |
| 4,966,552 | 10/1990 | Gonser . |
| 5,151,102 | 9/1992 | Kamiyama et al. . |
| 5,573,529 | 11/1996 | Hank et al. ........................ 606/1 |
| 5,801,110 | 9/1998 | Puglies et al. ........................ 501/87 |

FOREIGN PATENT DOCUMENTS

| 2760397 | 11/1978 | Germany . |
| 3107504 | 5/1982 | Germany . |
| 3610041 | 10/1986 | Germany . |
| 4017626 | 7/1993 | Germany . |
| 29502764 | 5/1995 | Germany . |
| 29509705 | 10/1995 | Germany . |

OTHER PUBLICATIONS

Patent Abstract of Japan –Publication No. 08033701, published Feb. 6, 1996.
Derwent Abstract for Japanese Patent 62200148, published Feb. 28, 1986.

Primary Examiner—Michael Buiz
Assistant Examiner—Vikki Trinh
Attorney, Agent, or Firm—Bachman & LaPointe, P.C.

[57] ABSTRACT

In the case of a surgical instrument for performing an operation, the surgical instrument is intended to consist of a ceramic material, preferably in one piece.

18 Claims, 1 Drawing Sheet

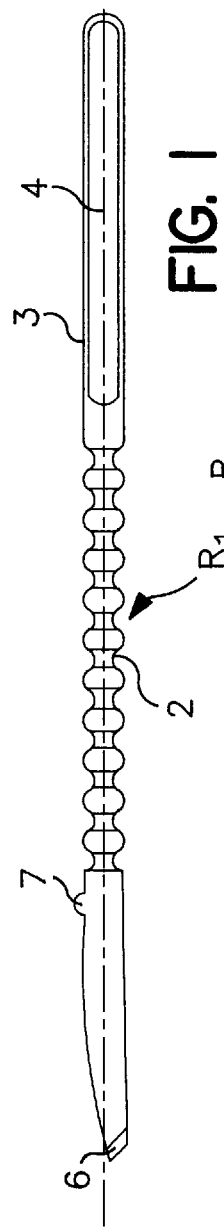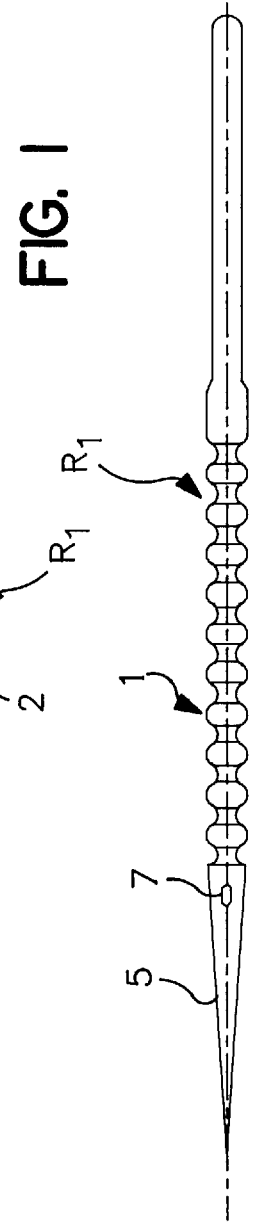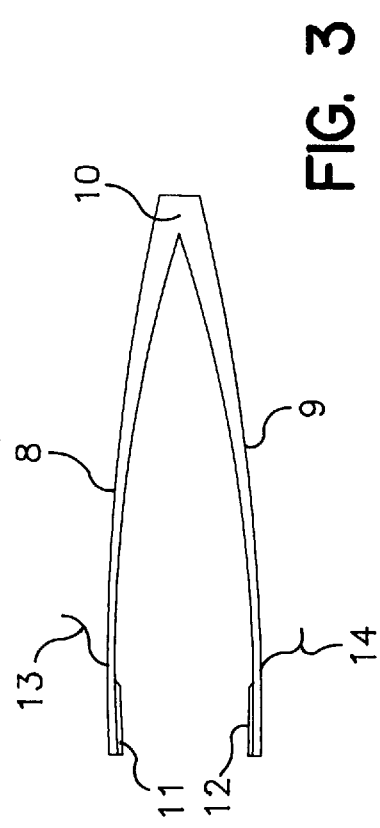

SURGICAL INSTRUMENT OF A CERAMIC MATERIAL AND PROCESS FOR FORMING SAME

BACKGROUND OF THE INVENTION

The present invention relates to a surgical instrument for performing operations.

Surgical instruments are available on the market in a variety of forms and designs. Generally used for surgical instruments are metallic materials, which are extremely expensive. Furthermore, metal also has further disadvantages with respect to hygiene requirements, since metal has a tendency to oxidize or the like. Furthermore, metallic surgical instruments must be cleaned and sterilized very intensively.

Disposable instruments in particular are currently produced at least partially from plastic. Known, for example, are disposable scalpels which have a plastic handle with a metal knife molded onto it. Diamond knives in a steel holder are also known. Since they are used only once, such surgical instruments are extremely expensive.

Furthermore, electric current is being used increasingly in surgery. Mention may be made just by way of example of electrocoagulation, in which high-frequency alternating currents are applied to destroy small areas of tissue. In this way, pedicellated polyps, ulcers and the like can be removed both from the outer skin and in body cavities. In electrocoagulation, a spark is produced, causing deep burning in an isolated point or line. This separates the tissue or attaches it (for example in the case of retinal detachment) and at the same time has a hemostatic effect by coagulation.

Even the sealing of blood vessels is generally performed today using so-called bipolar surgical instruments.

SUMMARY OF THE INVENTION

The present invention is based on the object of developing a surgical instrument of the above-mentioned type which is versatile in use and very inexpensive to produce.

Contributing to achieving this object is that the surgical instrument consists of a ceramic material, preferably in one piece.

The advantages of ceramic are sufficiently known. Ceramic materials are usually electrically nonconductive, have high strength, adequate resilience and are antiallergic. Furthermore, they do not become statically charged and can be combined with any desired materials. Moreover, ceramic is lighter than, for example, steel.

Particularly suitable as a ceramic material is zirconium dioxide or else a mixed oxide of zirconium dioxide and aluminum oxide. What is important is that the zirconium dioxide has a high bending moment, such as is required, for example, for surgical tweezers. A further advantage of zirconium dioxide is that it can change in color, so that the instrument can be colored as desired. However, the use of ceramic materials from silicon or, for example, nitride ceramic also appears to be possible.

It is known that, after diamond, certain ceramic materials are the hardest materials. Therefore, even a scalpel with a sharp blade can be formed from a ceramic material of the above-mentioned type. It is also possible to regrind this blade.

The surgical instrument is preferably produced by the injection process. This comprises using the injection-molding process to produce the surgical instrument in one piece from the ceramic material which has been mixed with a polymer component. Thereafter, the binder is removed from the finished product, i.e. the polymer component is filtered out by a specific process, which is known and involves using, for example, nitrogen and nitric acid. This is then followed by sintering of the surgical instrument.

This surgical instrument can be used in particular also to perform electrical or electronic operations. For electrocoagulation, such instruments can also be used in particular in electrical surgery. If, for example, a pair of tweezers is provided with an electrical coating in the front region of its two legs and this coating is connected to a corresponding current source, these tweezers can be used without any difficulties to seal blood vessels, without even any further electrical insulation of the instrument being necessary.

DESCRIPTION OF THE DRAWINGS

Further advantages, features and details of the invention emerge from the following description of preferred exemplary embodiments and with reference to the drawings, in which:

FIG. 1 shows a plan view of a surgical instrument according to the invention;

FIG. 2 shows a plan view of the surgical instrument according to FIG. 1, turned through 90°;

FIG. 3 shows a plan view of a further exemplary embodiment of a surgical instrument.

DETAILED DESCRIPTION OF PREFERRED EMBODIMENTS

According to FIGS. 1 and 2, shown as an example of a surgical instrument is a scalpel $R_1$, which according to the invention consists entirely of a ceramic material.

A central region 1 of the scalpel $R_1$ is provided with a plurality of grooves 2, which serve for better gripping of the scalpel $R_1$ by the surgeon.

The central region 1 is adjoined on one side by a shank portion 3, which is flattened on both sides. To save weight, depressions 4 may also be molded into this shank portion 3 on both sides.

On the other side of the central region 1, a wedged tip 5 of the scalpel $R_1$ tapers to a cutting edge 6, this cutting edge 6 preferably being ground.

Furthermore, on top of the wedged tip 5 there is a projecting sight 7, by means of which better-aimed use of the scalpel $R_1$ is possible.

Within the scope of the invention, the entire scalpel $R_1$ consists in one piece of a ceramic material, preferably of zirconium dioxide, aluminum oxide or a mixed-oxide ceramic. It is produced by the injection-molding process, polymer components present are removed and the instrument produced is then sintered.

By the same process, for example a pair of tweezers according to FIG. 3 can also be produced. This pair of tweezers $R_2$ is also produced in one piece by the injection-molding process, two legs 8 and 9 of the tweezers being connected to each other at one end 10. The ceramic material has adequate resilience, so that the legs 8 and 9 are always attempting to move into the open position.

In a preferred exemplary embodiment of the invention, the two legs 8 and 9 are provided in the front region with an electrically conductive coating 11 and 12, which have in each case an electrical connection 13 and 14. This turns the tweezers $R_2$ into a bipolar instrument, which can be used, for example, to fuse together blood vessels.

We claim:

1. A surgical one piece instrument for performing an operation, which comprises:

an operative forward region for performing an operation; a gripping region for holding the instrument by a user behind the forward region; and wherein said instrument consists entirely of injection molded ceramic material.

2. The instrument according to claim 1, wherein said ceramic is selected from the group consisting of zirconium dioxide, aluminum oxide, a mixed oxide of zirconium dioxide and aluminum oxide, a silicon ceramic, and a nitride ceramic.

3. The instrument according to claim 1, wherein said instrument is a scalpel with the operative forward region being a tip portion which is ground to form a cutting edge.

4. The instrument according to claim 3, wherein the tip is in the form of a wedge.

5. The instrument according to claim 4, including a sight means on said wedged tip.

6. The instrument according to claim 3, wherein the gripping region is a central region behind the forward region.

7. The instrument according to claim 6, wherein said central region includes a plurality of grooves to aid in gripping.

8. An instrument according to claim 6, including a shank region behind the central region, wherein said shank region includes two flattened sides.

9. The instrument according to claim 8, wherein said shank region includes depressions in each flattened side.

10. The instrument according to claim 1, wherein said instrument is a pair of tweezers including two legs connected to each other at a rear end of the instrument opposed to said forward region, wherein said legs have an open position with the legs spaced from each other, and wherein said ceramic material is resilient so that the legs attempt to move into the open position.

11. The instrument according to claim 10, wherein the operative forward region includes inside leg portions which face each other.

12. The instrument according to claim 11, wherein said forward region includes an electrically conductive coating.

13. Process for forming a surgical instrument, which comprises:

molding a surgical instrument entirely of injection molded ceramic material so that said instrument includes a forward region for performing an operation and a gripping region for holding the instrument by a user behind the forward region;

including the steps of mixing the ceramic material with a polymer binding component, molding the ceramic instrument from the mixture, removing the binding component from the molded product, and sintering the resultant instrument.

14. Process according to claim 13, wherein said ceramic material is selected from the group consisting of zirconium dioxide, aluminum oxide, a mixed oxide of zirconium dioxide and aluminum oxide, a silicon ceramic, and a nitride ceramic.

15. Process according to claim 13, including the step of molding a scalpel from the mixture with the operative forward region being a tip portion which is ground to form a cutting edge.

16. Process according to claim 13, including the step of molding a pair of tweezers from said mixture including two legs connected to each other at a rear end of the instrument opposed to said forward region, wherein said legs have an open position with the legs spaced from each other, and wherein said ceramic material is resilient so that the legs attempt to move into the open position.

17. Process according to claim 16, including the step of providing the operative forward region with inside leg portions which face each other.

18. Process according to claim 16, including the step of providing an electrically conductive coating on said forward region.

* * * * *